(12) United States Patent
Umar (10) Patent No.: US 10,357,278 B1
(45) Date of Patent: Jul. 23, 2019

(54) SLIT MAKER

(71) Applicant: Sanusi Umar, Redondo Beach, CA (US)

(72) Inventor: Sanusi Umar, Redondo Beach, CA (US)

( * ) Notice: Subject to any disclaimer, the term of this patent is extended or adjusted under 35 U.S.C. 154(b) by 288 days.

(21) Appl. No.: 14/932,984

(22) Filed: Nov. 5, 2015

(51) Int. Cl.
*A61F 9/007* (2006.01)
*A61B 17/3209* (2006.01)
*A61B 17/00* (2006.01)

(52) U.S. Cl.
CPC ........ A61B 17/32093 (2013.01); A61F 9/007 (2013.01); *A61B 2017/00752* (2013.01)

(58) Field of Classification Search
CPC ........... A61F 9/007; A61B 2017/00752; A61B 17/32093; A61B 2017/06076; A61B 17/2018; A61B 17/32; A61B 2017/00747; A61B 2017/00792; A61B 90/02; A61B 2017/320044; A61M 25/0041; A61M 25/0068; A61M 25/0082
See application file for complete search history.

(56) References Cited

U.S. PATENT DOCUMENTS

| | | | |
|---|---|---|---|
| 5,209,755 A | 5/1993 | Abrahan et al. | |
| 5,578,054 A | 11/1996 | Arnold | |
| 6,471,709 B1 | 10/2002 | Fawzi et al. | |
| 8,211,116 B2 | 7/2012 | Oostman, Jr. et al. | |
| 8,343,075 B2 | 1/2013 | Freeman et al. | |
| 8,876,847 B2 | 11/2014 | Umar | |
| 9,017,343 B2 | 4/2015 | Westerling, Jr. et al. | |
| 2004/0092924 A1 | 5/2004 | Vasa | |
| 2005/0049622 A1 | 3/2005 | Mittelstaeot | |
| 2006/0241673 A1* | 10/2006 | Zadini ................ | A61B 17/0218 606/192 |
| 2007/0005091 A1* | 1/2007 | Zadini ................... | A61B 17/32 606/192 |
| 2011/0046639 A1 | 2/2011 | Giotis | |
| 2011/0251602 A1 | 10/2011 | Anderson et al. | |

FOREIGN PATENT DOCUMENTS

| | | |
|---|---|---|
| GB | 222882 A | 9/1990 |
| WO | 2005122721 A2 | 12/2005 |
| WO | 2005122721 A3 | 7/2007 |
| WO | 2010131270 A1 | 11/2010 |

* cited by examiner

*Primary Examiner* — George J Ulsh
(74) *Attorney, Agent, or Firm* — Law Office of Michael O'Brien (57) ABSTRACT

A slit maker is configured to make a slit in skin to receive a hair follicle. The slit maker has a shaft, having a shaft central axis. A helix is mechanically coupled to the shaft. A tip is at an end of the helix. An edge is beveled onto the tip being collinear to an edge line. An edge angle is measured from the edge line to the shaft central axis. The edge angle is at least 10 degrees but no more than 60 degrees or least 130 degrees but no more than 170 degrees.

19 Claims, 12 Drawing Sheets

SLIT MAKER

BACKGROUND

The embodiments herein relate generally to tool for implanting and transplanting hair.

The eyelash is a hair follicle extending from the eyelid. A portion of the eyelash beneath the skin on the eyelid is near the glands of Zeis and Moll's gland. In some cases, the eyelashes fall out in conditions such as Madarosis. Prior to embodiments of the disclosed invention, replacing eyelashes lacked a simple solution because there was no good device to create a slit into which a follicle could be inserted. While there is no directly analogous technology, some other efforts in the field of hair grafting include: WIPO Publication 2010/131270 filed by Nobbio; U.S. Patent application pre grant publication 2004/0092924 filed by Vasa; U.S. Pat. No. 6,471,709 issued to Fawzi; U.S. Pat. No. 8,876,847 issued to Umar; U.S. Patent application pre grant publication 2005/0049622 filed by Mittelstaeot; U.S. Pat. No. 5,209,755 issued to Abrahan; U.S. patent application pre grant publication 2011/0251602 filed by Anderson; WIPO Publication 2003/070088 filed by Tschakaloff; U.S. Pat. No. 5,578,054 issued to Arnold; U.S. Pat. No. 9,017,343 issued to Westerling; U.S. Pat. No. 8,211,116 issued to Oostman; U.S. Pat. No. 8,343,075 issued to Freeman; Great Brian Patent 2,228,872 issued to Tatsya, and WIPO Publication 2005/122721 filed by Evans.

Evans teaches an instrument for performing a surgical technique that uses a helical applicator in one embodiment which is shown to the right. The dimensions provided for Evans, where L-29 is two to five inches, is much too large for inserting hair.

Nobbio teaches an instrument for puncturing the skin for hair transplant operations. Nobio has a handle attached to a rotating tube that rotates about a central axis of the tube. The tube has a series of sharp tips that puncture the skin when rotated. The rotation is about a single axis and is not helical. Nobio nonetheless concludes that the tool could be used for eyebrow. Anderson, in one embodiment, uses a similar roller arrangement, but argues that other kinds of blade arrangements can be more effective.

Vasa teaches a tool that is useful both for extracting and transplanting hair. Vasa's tool has a tube with an opening in the front above a blade such that the blade can cut a slit around the hair to remove the hair through the opening. Umar teaches the distal edges of the cutting tool opening from one another without a central opening as in Vasa. Umar teaches a helical textured region, but not a helical cutting path. Freeman uses a helical tube that moves parallel to the lancet to hold the slit open.

Fawzi teaches a hair removal tool that has a cutting member with edges which concentrically collapse upon them self or by movement of a distal edge on the tool. Mittelstaet teaches a plurality of blades extending through the tool. Arnold has a single blade and recommends it be inserted deeper than the others. Westerling advocates for a non-circular tip similar to Fawzi. Oostman is similar but uses concave edges on its tip. Tatsya uses concentric cutting surfaces that telescope from one another.

Abrahan teaches a linkage device for removing portions of skin, but offers no real theory about applicability to hair. Tschakaloff teaches manipulating and sewing skin into place to lift eyebrows, but is more interested with manipulating skin than removing hair.

SUMMARY

A slit maker is configured to make a slit in skin to receive a hair follicle. The slit maker has a shaft, having a shaft central axis. A helix is mechanically coupled to the shaft. A tip is at an end of the helix. An edge is beveled onto the tip being collinear to an edge line. An edge angle is measured from the edge line to the shaft central axis. In some embodiments, the edge angle can be at least 10 degrees but no more than 60 degrees or least 130 degrees but no more than 170 degrees.

In some embodiments, the shaft further comprises a first shaft bend section. The first shaft bend section has a first shaft bend entry central axis that is the same as the shaft central axis and a first shaft bend exit central axis that is rotationally offset from the shaft central axis by a shaft first angle. The shaft first angle is at least 30 degrees but no more than 150 degrees.

In some embodiments, a shaft straight section is joined to the first shaft bend section. The shaft straight section has a central axis collinear with the first shaft bend exit central axis.

In some embodiments, a second bend section is joined to the shaft straight section. The second bend section has a second bend section entry central axis collinear to the first shaft bend exit central axis. The second bend section has a second bend section exit central axis. A second offset angle is measured from the first shaft bend exit central axis to the second bend section exit central axis. The second offset angle is at least 90 degrees but no more than 180 degrees.

The helix can further comprise a helical centroid which is part of a helical plane. The shaft central axis passes through the helical plane at a helical intersection angle. The helical intersection angle is at least 45 degrees but no more than 135 degrees.

The edge extends from the edge line to a rounded edge at a sharpened angle that, when measured from the helix to the edge line along the rounded edge is at least 5 degrees but no more than 30 degrees. A rear side of the rounded edge truncates to a point from a truncated tip. A truncated tip angle is measured from a portion of the helix that extends to the back side. The truncated tip angle is at least 30 degrees but no more than 90 degrees.

A process for making a slit on an eyelid in order to insert a hair follicle includes the following steps, which are not necessarily in order. First, establishing a reference line that is parallel to and offset from a distal edge of the eyelid. Then, providing a slit maker further comprising: a shaft, having a shaft central axis; a helix, mechanically coupled to the shaft; a tip at an end of the helix; and an edge beveled onto the tip being collinear to an edge line. After that, inserting the edge at a slit entrance point. Following that, rotating the slit maker to create the slit having a slit central axis.

In some embodiments, the process can further include creating a slit entrance angle measured from the reference line to the slit central axis. In some embodiments, the slit entrance angle can be at least 0 degrees but no more than 90 degrees. In some embodiments, the slit entrance angle can be about 12.5 degrees. In some embodiments, the slit entrance angle can be at least 90 degrees but no more than 270 degrees. In some embodiments, the slit entrance angle can be about 167.5 degrees.

BRIEF DESCRIPTION OF THE FIGURES

The detailed description of some embodiments of the invention is made below with reference to the accompanying figures, wherein like numerals represent corresponding parts of the figures.

DETAILED DESCRIPTION OF CERTAIN EMBODIMENTS

Figure 1:
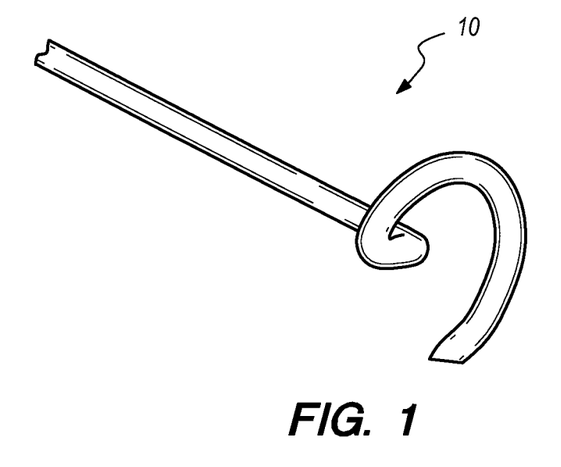
FIG. 1 shows a perspective view of an embodiment of the present invention.
Figure 2:
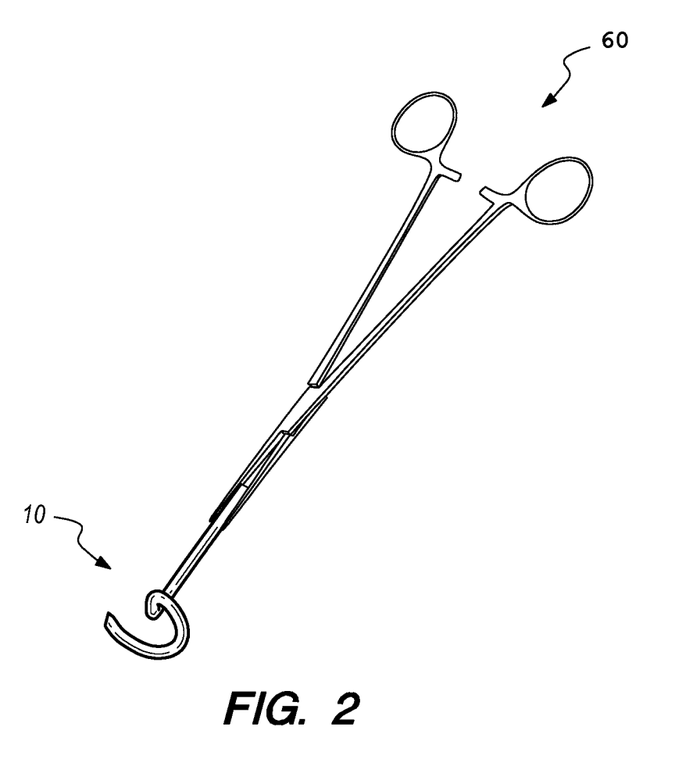
FIG. 2 shows a perspective view in use of an embodiment of the present invention.
Figures 3A, 3B:
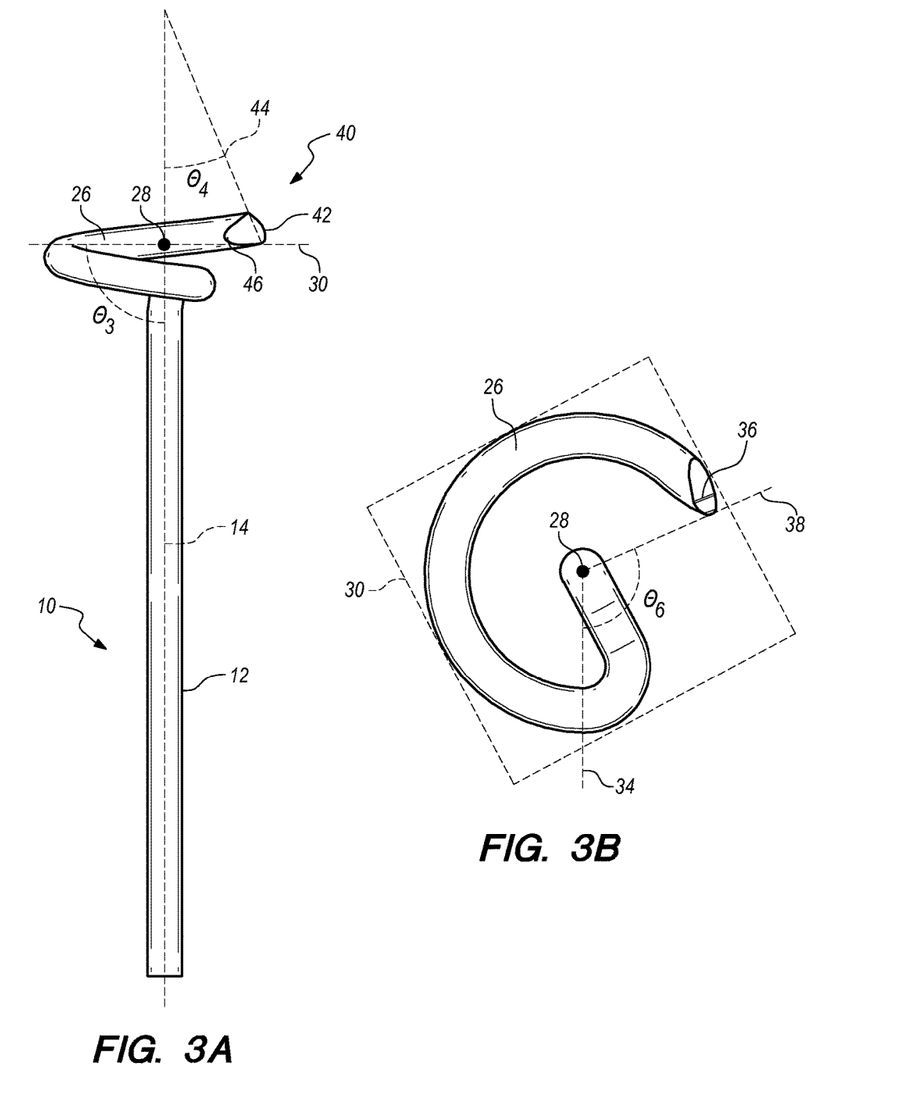
FIG. 3A shows a front view of an embodiment of the invention.
FIG. 3B shows a top view of an embodiment of the invention.
Figures 3C, 3D:
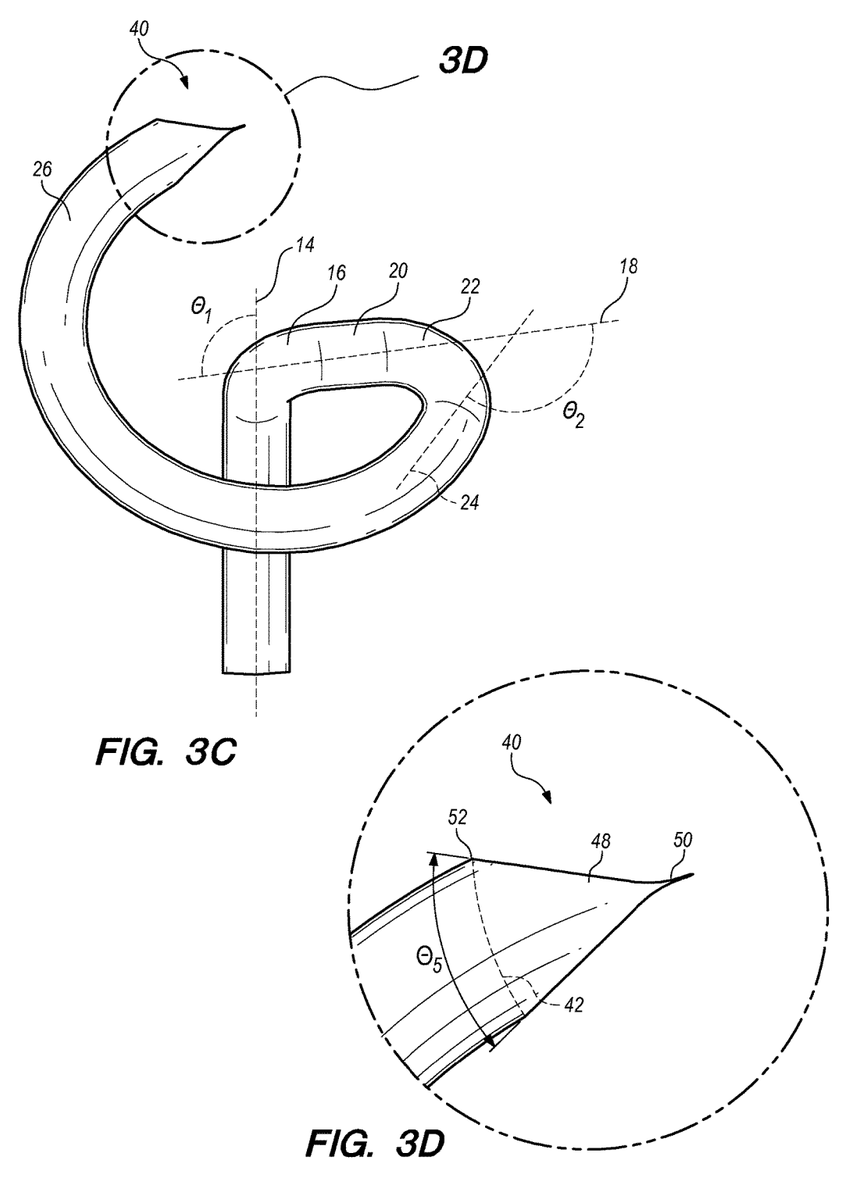
FIG. 3C shows a side view of an embodiment of the invention.
FIG. 3D shows a side view of an embodiment of the invention.
Figure 4A:
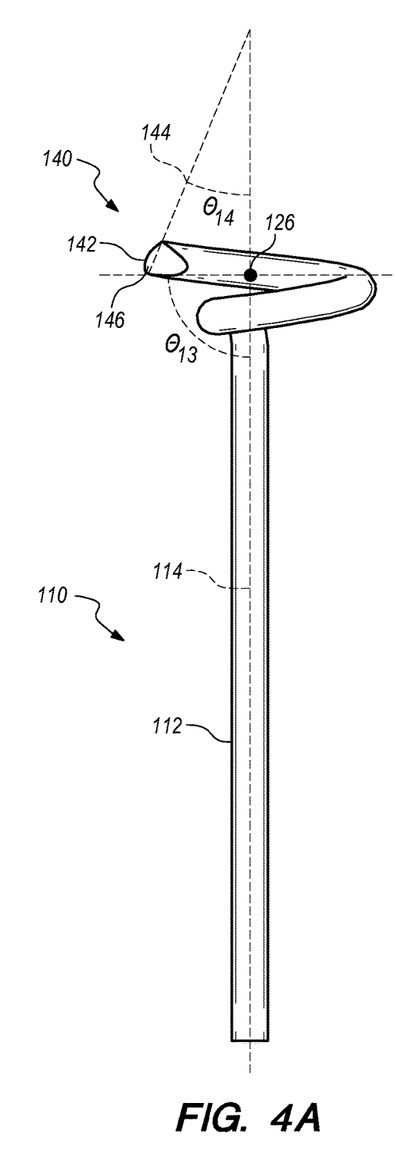
FIG. 4A shows a front view of an embodiment of the invention.
Figure 4B:
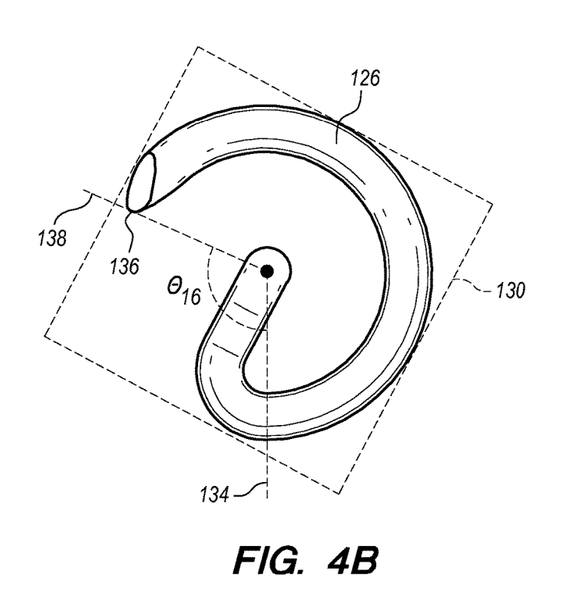
FIG. 4B shows a top view of an embodiment of the invention.
Figure 4C:
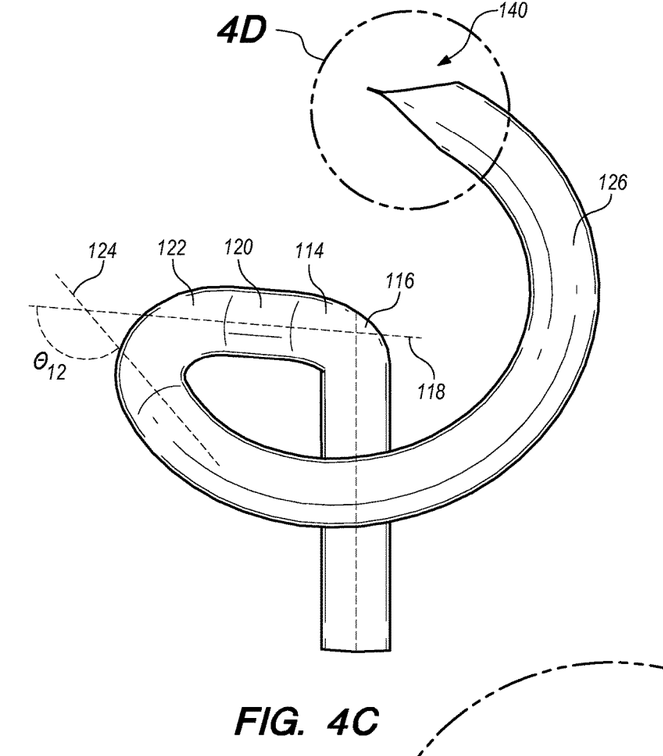
FIG. 4C shows a side view of an embodiment of the invention.
Figure 4D:
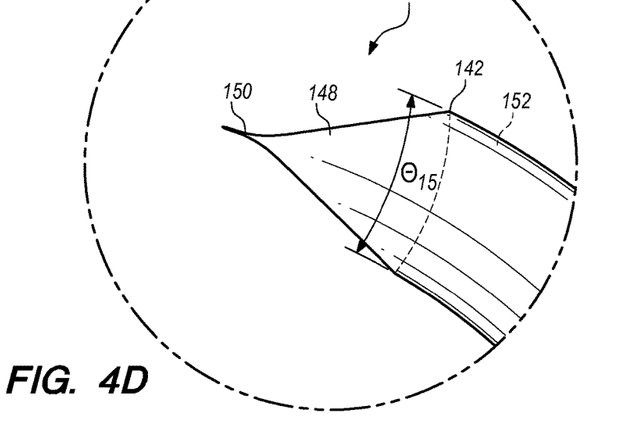
FIG. 4D shows a side view of an embodiment of the invention.
Figures 5A, 5B:
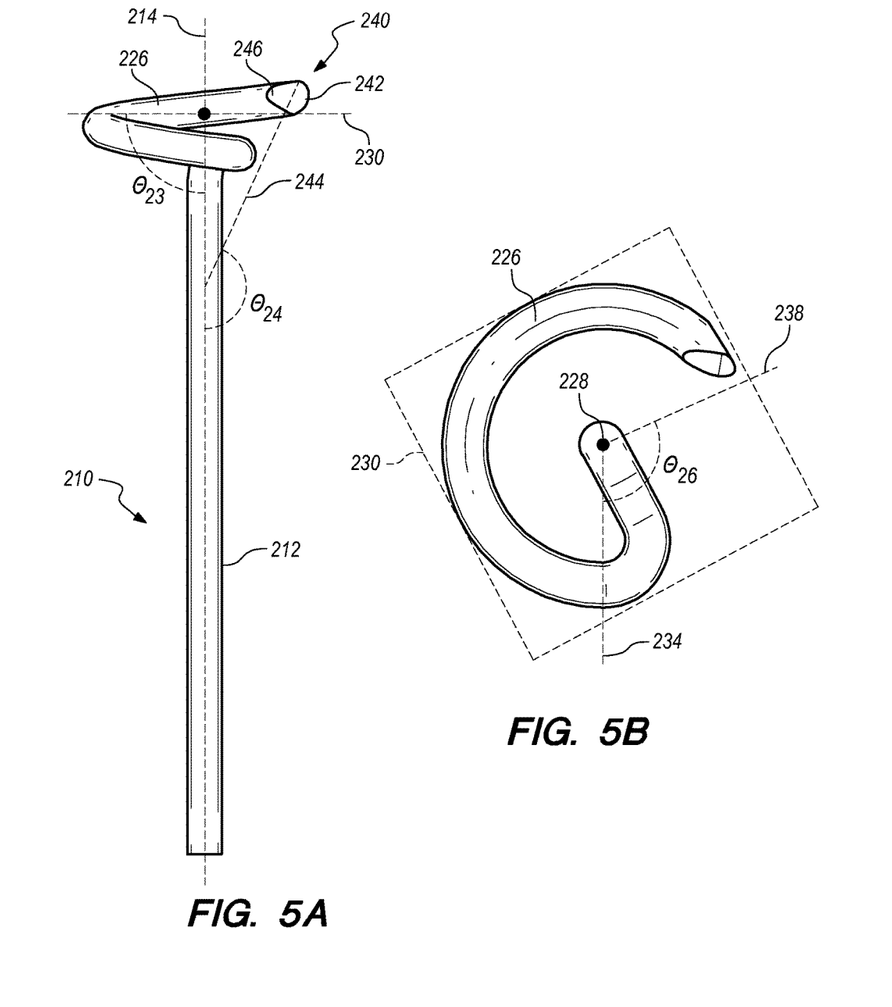
FIG. 5A shows a front view of an embodiment of the invention.
FIG. 5B shows a top view of an embodiment of the invention.
Figure 5C:
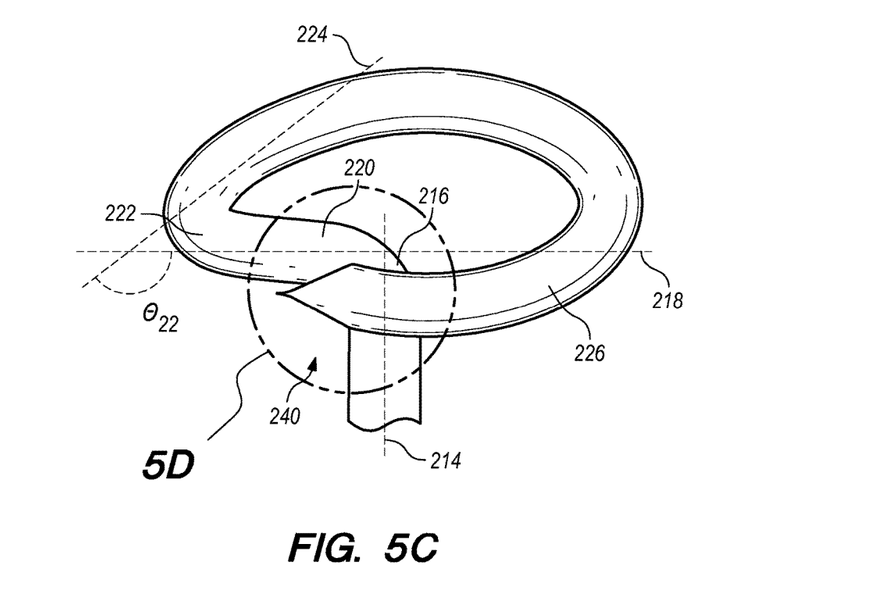
FIG. 5C shows a side view of an embodiment of the invention.
Figure 5D:
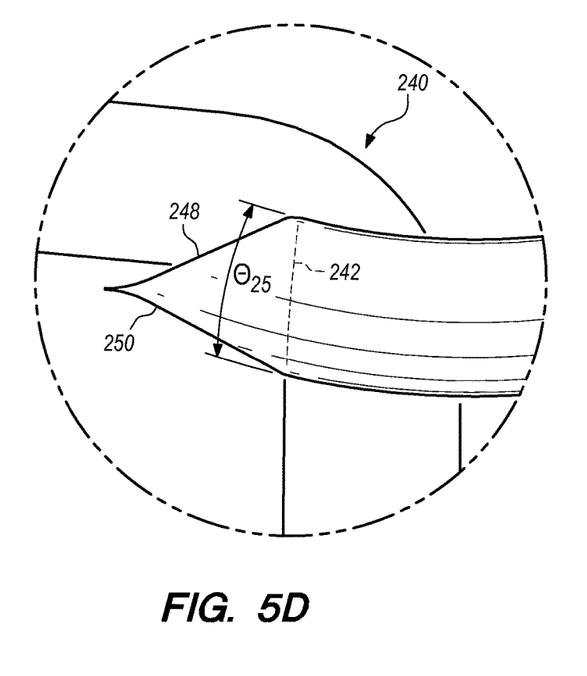
FIG. 5D shows a side view of an embodiment of the invention.
Figure 6A:
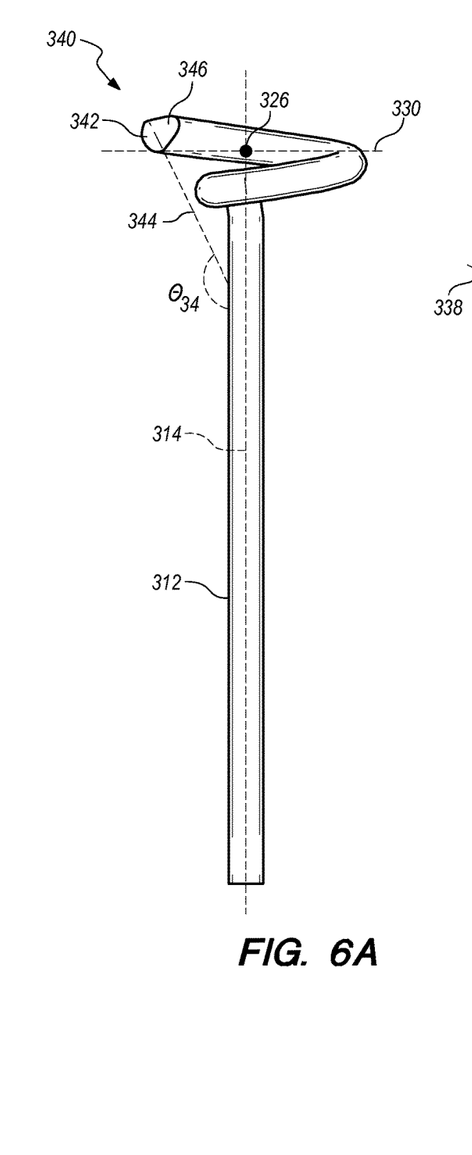
FIG. 6A shows a front view of an embodiment of the invention.
Figure 6B:
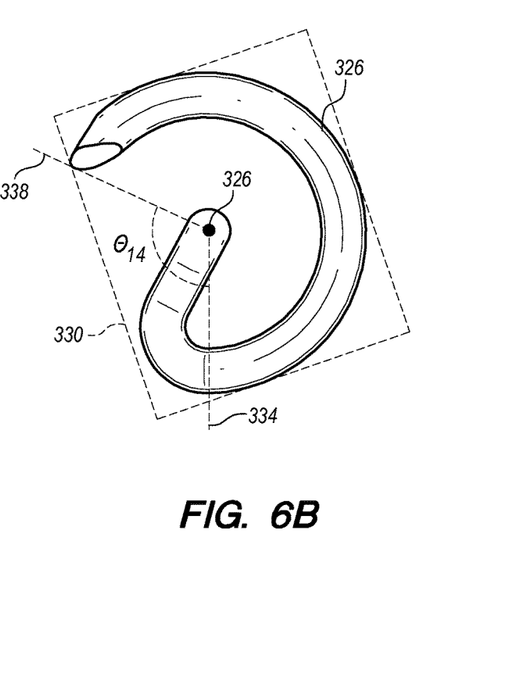
FIG. 6B shows a top view of an embodiment of the invention.
Figures 6C, 6D:
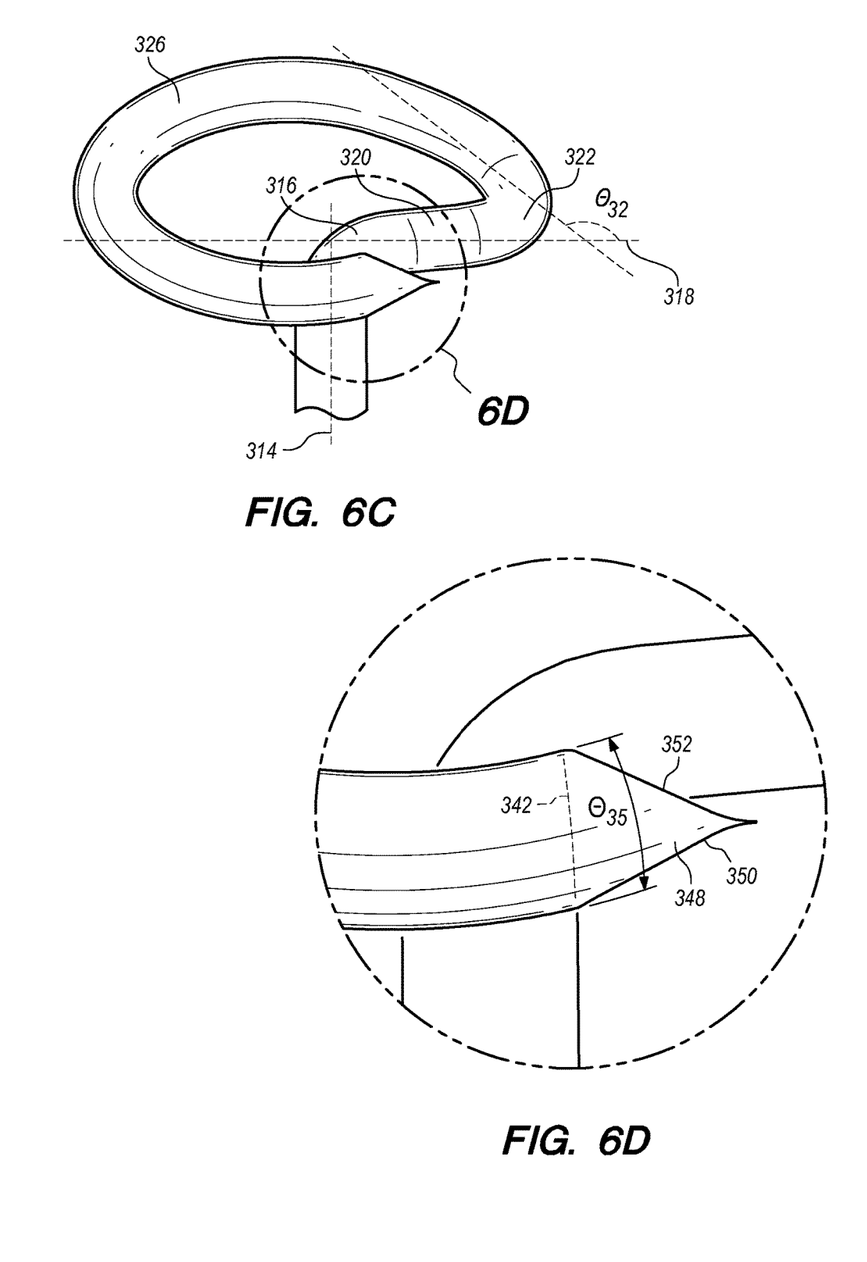
FIG. 6C shows a side view of an embodiment of the invention.
FIG. 6D shows a side view of an embodiment of the invention.

By way of example, and referring to FIGS. 1 and 2, one embodiment of slit maker 10 could be used manually by a physician. In another possible usage, a pair of forceps 60 could be used to hold slit maker 10.

FIGS. 3A, 3B, 3C, and 3D show a right handed slit maker for use on a right eyelid. Slit maker 10 further comprises shaft 12. Shaft 12 is shown as a tube having shaft central axis 14. Shaft 12 is joined to first shaft bend section 16 which has a first shaft bend entry central axis that is the same as shaft central axis 14 and a first shaft bend exit central axis 18 that is offset from shaft central axis 14 by shaft first angle θ1. First shaft bend section 16 is joined to shaft straight section 20 which has a central axis collinear with first shaft bend exit central axis 18. Shaft straight section 20 is joined to second bend section 22. Second bend section 22 has a second bend section entry central axis collinear to first shaft bend exit central axis 18. Second bend section 22 has a second bend section exit central axis 24. Measuring from the first shaft bend exit central axis 18, second bend section exit central axis 24 is offset by second offset angle θ2.

Second bend section 22 is joined to helix 26. Helix 26 further comprises helical centroid 28 which is part of helical plane 30. Shaft central axis 14 passes through helical plane 30 and helical intersection angle θ3. From helical centroid 28, helical beginning point 32 is connected with helical entrance line 34. From helical centroid 28, tip point 36 is connected with tip line 38. Helical angular truncated tip θ6 is measured from helical entrance line 34 to tip line 38.

Tip 40 is at the end of helix 26. Tip 40 further comprises edge 42. Edge 42 has a first end that is collinear with edge line 44. Edge line 44 intersects shaft central axis 14 at an edge angle θ4. Next to edge 42 is rounded edge 46. Rounded edge 46 is a beveled portion of helix 26 that extends from edge line 42. In some embodiments, rounded edge 46 is sharpened at sharpened angle, that when measured from helix 26 to edge line 44 along rounded edge 46 is 5 to 30 degrees or preferable about 15 degrees. A rear side 48 of rounded edge 46 truncates to a point 50 from a truncated tip 52. The angular portion of the truncated tip of the 360 degree of the tube that forms helix 26 is represented by truncated tip angle θ5.

Slit maker 10 is a right handed tool for use on a right eyelid. For this to be effective shaft first angle θ1 should be 30 to 150 degrees, but preferably about 90 degrees. Second offset angle θ2 should be 90 to 180 degrees, but preferably about 120 degrees. Helical intersection angle θ3 should be 45 to 135 degrees, but preferably about 90 degrees. Edge angle θ4 can be 10 to 60 degrees, but preferably about 35 degrees. Truncated tip angle θ5 can be 30 to 90 degrees, but preferably about 52 degrees. Helical angular truncated tip θ6 is between 180 degrees and 360 degrees and is preferably 240 degrees.

FIGS. 4A, 4B, 4C, and 4D show a left handed slit maker for use on a left eyelid. Slit maker 110 further comprises shaft 112. Shaft 112 is shown as a tube having shaft central axis 114. Shaft 112 is joined to first shaft bend section 116 which has a first shaft bend entry central axis that is the same as shaft central axis 114 and a first shaft bend exit central axis 118 that is offset from shaft central axis 114 by shaft first angle θ11. First shaft bend section 116 is joined to shaft straight section 120 which has a central axis collinear with first shaft bend exit central axis 118. Shaft straight section 120 is joined to second bend section 122. Second bend section 122 has a second bend section entry central axis collinear to first shaft bend exit central axis 118. Second bend section 122 has a second bend section exit central axis 124. Measuring from the first shaft bend exit central axis 118, second bend section exit central axis 124 is offset by second offset angle θ12.

Second bend section 122 is joined to helix 126. Helix 126 further comprises helical centroid 128 which is part of helical plane 130. Shaft central axis 114 passes through helical plane 130 and helical intersection angle θ13. From helical centroid 128, helical beginning point 132 is connected with helical entrance line 134. From helical centroid 128, tip point 136 is connected with tip line 138.

Tip 140 is at the end of helix 126. Tip further comprises edge 142. Edge 142 has a first end that is collinear with edge line 144. Edge line 144 intersects shaft central axis 114 at an edge angle θ14. Next to edge 142 is rounded edge 146. Rounded edge 146 is a beveled portion of helix 126 that extends from edge 142. A rear side 148 of rounded edge 146 truncates to a point 150 from a truncated tip 152. The angular portion of the truncated tip of the 360 degree of the tube that forms helix 126 is represented by truncated tip angle θ15.

Slit maker 110 is a left handed tool for use on a left eyelid. For this to be effective shaft first angle θ11 should be 30 to 150 degrees, but preferably about 90 degrees. Second offset angle θ12 should be 90 to 180 degrees, but preferably about 120 degrees. Helical intersection angle θ13 should be 45 to 135 degrees, but preferably about 90 degrees. Edge angle θ14 can be 10 to 60 degrees, but preferably about 35 degrees. Truncated tip angle θ15 can be 30 to 90 degrees, but preferably about 52 degrees.

FIGS. 5A, 5B, 5C, and 5D show a right handed slit maker for use on a left eyelid. Slit maker 210 further comprises shaft 212. Shaft 212 is shown as a tube having shaft central axis 214. Shaft 212 is joined to first shaft bend section 216 which has a first shaft bend entry central axis that is the same as shaft central axis 214 and a first shaft bend exit central axis 218 that is offset from shaft central axis 214 by shaft first angle θ21. First shaft bend section 216 is joined to shaft straight section 220 which has a central axis collinear with first shaft bend exit central axis 218. Shaft straight section 220 is joined to second bend section 222. Second bend section 222 has a second bend section entry central axis collinear to first shaft bend exit central axis 218. Second bend section 222 has a second bend section exit central axis 224. Measuring from the first shaft bend exit central axis 218, second bend section exit central axis 224 is offset by second offset angle θ22.

Second bend section 222 is joined to helix 226. Helix 226 further comprises helical centroid 228 which is part of helical plane 230. Shaft central axis 214 passes through helical plane 230 and helical intersection angle θ23. From helical centroid 228, helical beginning point 232 is connected with helical entrance line 234. From helical centroid 228, tip point 236 is connected with tip line 238.

Tip 240 is at the end of helix 226. Tip further comprises edge 242. Edge 242 has a first end that is collinear with edge line 244. Edge line 244 intersects shaft central axis 214 at an edge angle θ24. Next to edge 242 is rounded edge 246. Rounded edge 246 is a beveled portion of helix 226 that extends from edge 242. A rear side 248 of rounded edge 246 truncates to a point 250 from a truncated tip 252. The angular portion of the truncated tip of the 360 degree of the tube that forms helix 226 is represented by truncated tip angle θ25.

Slit maker 210 is a right handed tool for use on a left eyelid. For this to be effective shaft first angle θ21 should be 30 to 150 degrees, but preferably about 90 degrees. Second offset angle θ22 should be 90 to 180 degrees, but preferably about 120 degrees. Helical intersection angle θ23 should be 45 to 135 degrees, but preferably about 90 degrees. Edge angle θ24 can be 130 to 170 degrees, but preferably about 145 degrees. Truncated tip angle θ25 can be 30 to 90 degrees, but preferably about 52 degrees.

FIGS. 6A, 6B, 6C, and 6D show a left handed slit maker for use on a right eyelid. Slit maker 310 further comprises shaft 312. Shaft 312 is shown as a tube having shaft central axis 314. Shaft 312 is joined to first shaft bend section 316 which has a first shaft bend entry central axis that is the same as shaft central axis 314 and a first shaft bend exit central axis 318 that is offset from shaft central axis 314 by shaft first angle θ31. First shaft bend section 316 is joined to shaft straight section 320 which has a central axis collinear with first shaft bend exit central axis 318. Shaft straight section 320 is joined to second bend section 322. Second bend section 322 has a second bend section entry central axis collinear to first shaft bend exit central axis 318. Second bend section 322 has a second bend section exit central axis 334. Measuring from the first shaft bend exit central axis 318, second bend section exit central axis 334 is offset by second offset angle θ32.

Second bend section 322 is joined to helix 326. Helix 326 further comprises helical centroid 328 which is part of helical plane 230. Shaft central axis 314 passes through helical plane 230 and helical intersection angle θ33. From helical centroid 328, helical beginning point 332 is connected with helical entrance line 334. From helical centroid 328, tip point 336 is connected with tip line 338.

Tip 340 is at the end of helix 326. Tip further comprises edge 342. Edge 342 has a first end that is collinear with edge line 344. Edge line 344 intersects shaft central axis 314 at an edge angle θ34. Next to edge 342 is rounded edge 346. Rounded edge 346 is a beveled portion of helix 326 that extends from edge 342. A rear side 348 of rounded edge 346 truncates to a point 350 from a truncated tip 352. The angular portion of the truncated tip of the 360 degree of the tube that forms helix 326 is represented by truncated tip angle θ35.

Slit maker 310 is a right handed tool for use on a left eyelid. For this to be effective shaft first angle θ31 should be 30 to 150 degrees, but preferably about 90 degrees. Second offset angle θ32 should be 90 to 180 degrees, but preferably about 120 degrees. Helical intersection angle θ33 should be 45 to 135 degrees, but preferably about 90 degrees. Edge angle θ34 can be 130 to 170 degrees, but preferably about 145 degrees. Truncated tip angle θ35 can be 30 to 90 degrees, but preferably about 52 degrees.

Figure 7:
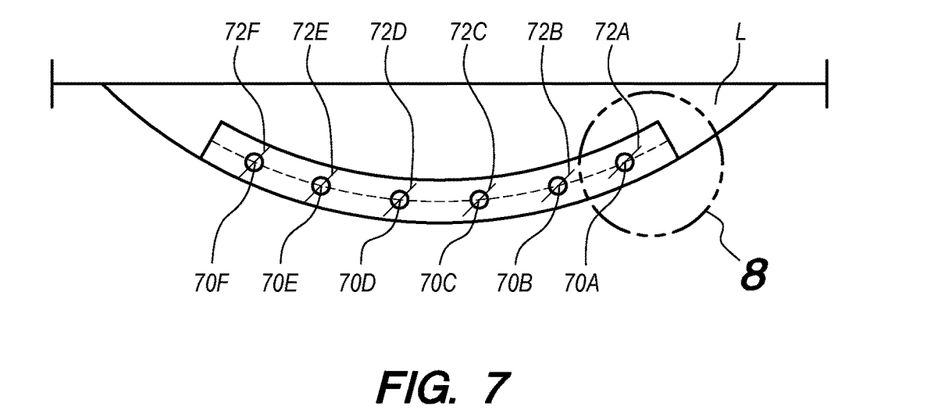
FIG. 7 is a perspective view of an eyelid.
Figure 8:
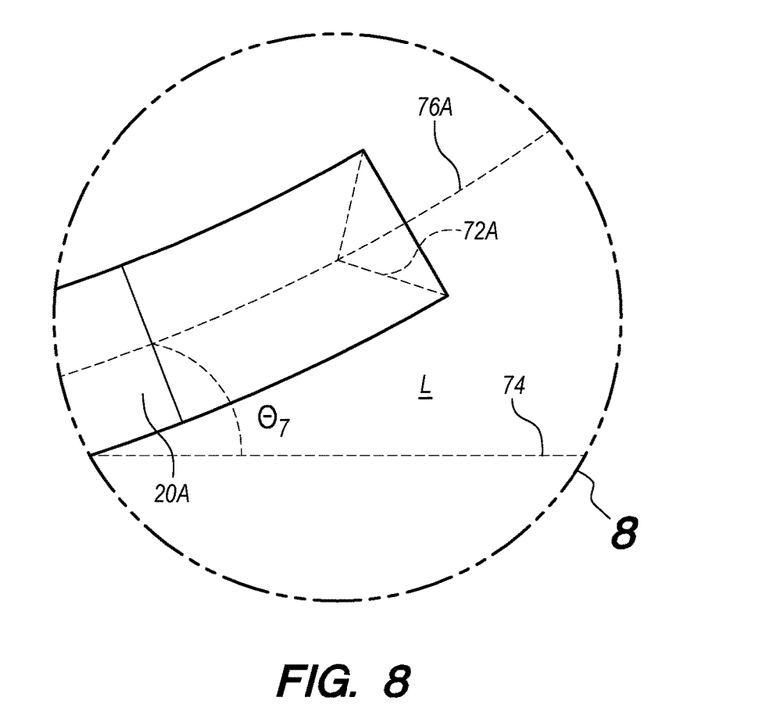
FIG. 8 is a perspective view of an eyelid.

Turning to FIG. 7 and FIG. 8, eyelid L is shown. A process can assist a user in making a slit 72 at a slit entrance point 70. A user can use the appropriate tool above given a dominant hand (left or right) and an eyelid (left or right). Then the user inserts the appropriate slit maker 10, 110, 210, 310 into eyelid L at slit entrance point 70A making a first slit 72A into eyelid E. The user does this by rotating the dominant hand from entrance point 70A into eyelid E. Reference line 74 is parallel to and offset from a distal edge of eyelid E. First slit 72A further comprises a first slit central axis 76A. Slit entrance angle θ7 can be measured from reference line 74 to first slit central axis 76A. In some embodiments on the left eyelid, slit entrance angle θ7 is between 90 and 270 degrees, but preferably about 167.5 degrees. In some embodiments on the right eyelid, slit entrance angle θ7 is between 0 and 90 degrees, but preferably about 12.5 degrees.

In a typical application one or more slits 72 may be necessary. Along reference line 74, slit maker 10, 110, 210, 310 is inserted into eyelid L at first slit entrance point 70A making a first slit 72A into eyelid E. Next, slit maker 10, 110, 210, 310 is inserted into eyelid L at second slit entrance point 70B making a second slit 72B into eyelid E. After that, slit maker 10, 110, 210, 310 is inserted into eyelid L at a third slit entrance point 70C making a third slit 72C into eyelid E. Following that, slit maker 10, 110, 210, 310 is inserted into eyelid L at a fourth slit entrance point 70D making a fourth slit 72D into eyelid E. Then, slit maker 10, 110, 210, 310 is inserted into eyelid L at a fifth slit entrance point 70E making a fifth slit 72E into eyelid E. Following that, slit maker 10, 110, 210, 310 is inserted into eyelid L at slit sixth entrance point 70F making a third slit 72F into eyelid E.

Figure 9A:
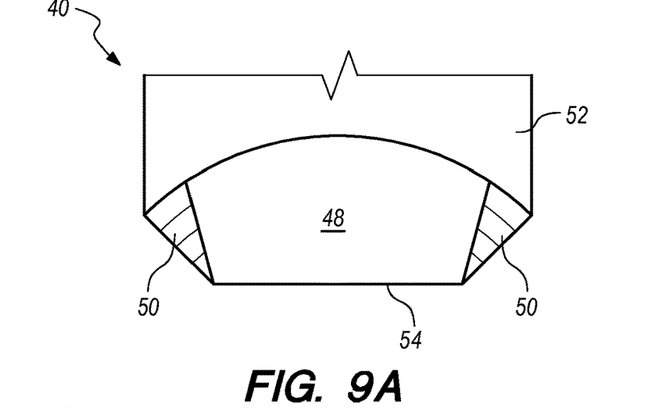
FIG. 9A is a detail view of an embodiment of the invention.
Figure 9B:
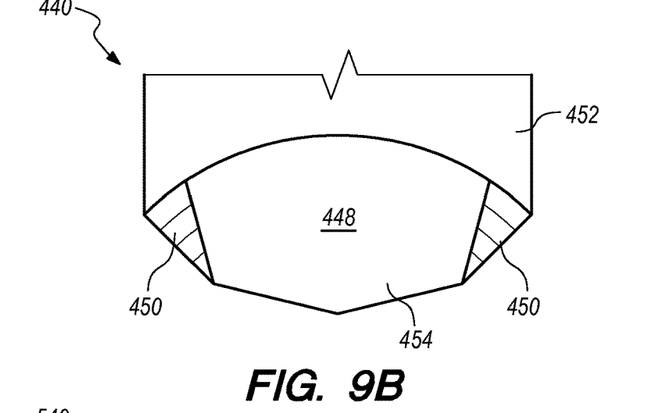
FIG. 9B is a detail view of an embodiment of the invention.
Figure 9C:
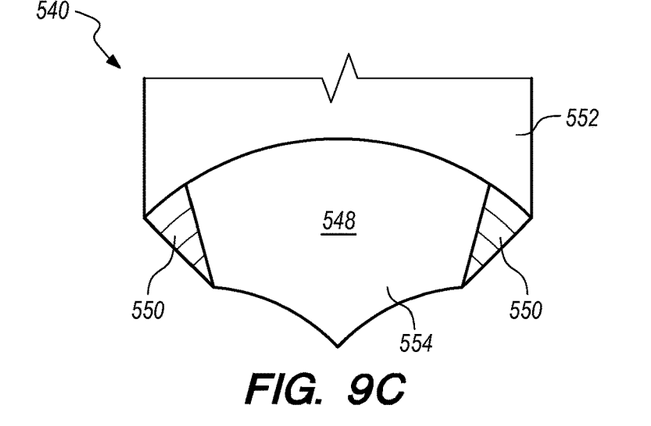
FIG. 9C is a detail view of an embodiment of the invention.

Turning to FIGS. 9A, 9B and 9C there are a plurality of different kinds of tips that can be effective. The first is tip 40 that further comprises truncated tip 52. Truncated tip 52 has rear side 48 that is adjacent to first point 50 and second point 50 at respective sides that terminate at flat point edge 54. The second is tip 440 that further comprises truncated tip 452. Truncated tip 452 has rear side 448 that is adjacent to first point 450 and second point 450 at respective sides that terminate at straight point edge 454. The third is tip 540 that further comprises truncated tip 552. Truncated tip 552 has rear side 548 that is adjacent to first point 550 and second point 550 at respective sides that terminate at rounded point edge 554. Additionally, the tip can be made from any shape provided the net result is a substantially straight slit that is made at the angles to the eyelid margin explained above.

Figure 10:
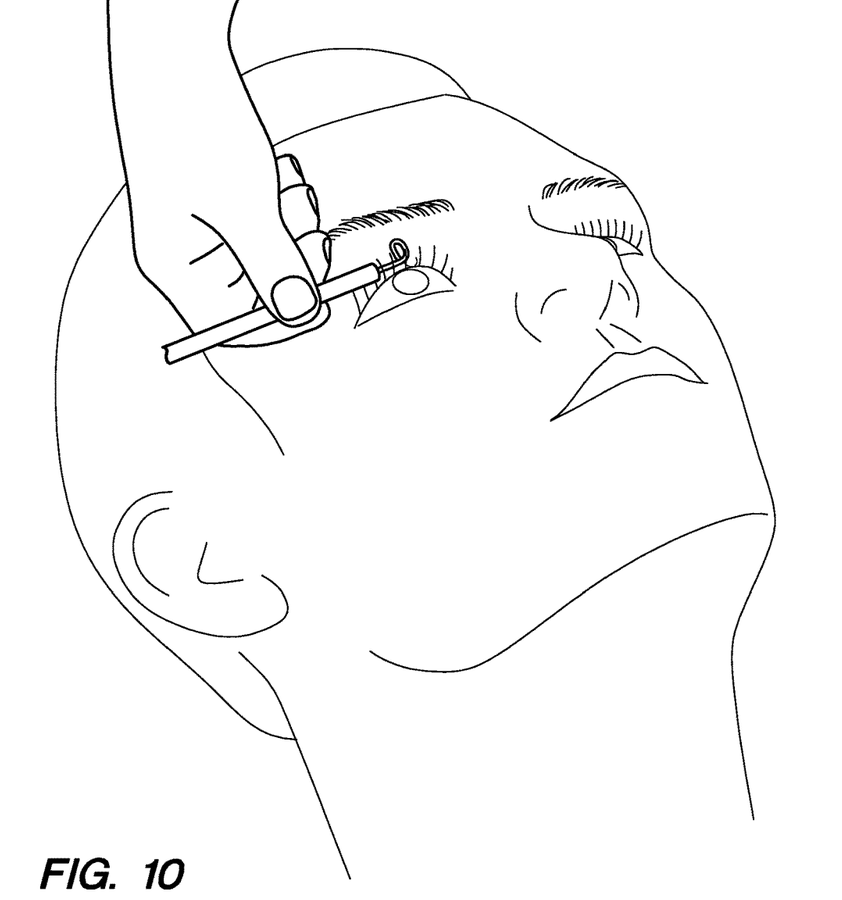
FIG. 10 is a perspective view of an embodiment of the invention shown in use.
Figure 11:
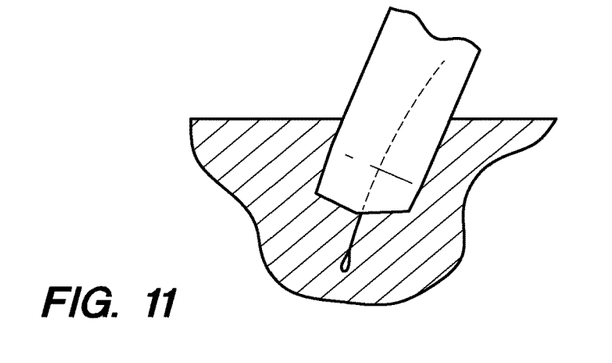
FIG. 11 is a section view of an embodiment of the invention shown in use.

FIG. 10 and FIG. 11 show an embodiment of this procedure in use. Here, a user is inserting slit maker 10, 110, 210, 310 is into eyelid L to make a slit for a hair follicle.

To use the device, a user simply selects the correct tool for the correct eyelid, knowing the user's dominant hand. The user then rotates the slit maker into the eyelid margins making a slit for a hair follicle.

As used in this application, the term "a" or "an" means "at least one" or "one or more."

As used in this application, the term "about" or "approximately" refers to a range of values within plus or minus 10% of the specified number.

As used in this application, the term "substantially" means that the actual value is within about 10% of the actual desired value, particularly within about 5% of the actual desired value and especially within about 1% of the actual desired value of any variable, element or limit set forth herein.

All references throughout this application, for example patent documents including issued or granted patents or equivalents, patent application publications, and non-patent literature documents or other source material, are hereby incorporated by reference herein in their entireties, as though individually incorporated by reference, to the extent each reference is at least partially not inconsistent with the disclosure in the present application (for example, a reference that is partially inconsistent is incorporated by reference except for the partially inconsistent portion of the reference).

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

Any element in a claim that does not explicitly state "means for" performing a specified function, or "step for" performing a specified function, is not to be interpreted as a "means" or "step" clause as specified in 35 U.S.C. § 112, ¶6. In particular, any use of "step of" in the claims is not intended to invoke the provision of 35 U.S.C. § 112, ¶6.

Persons of ordinary skill in the art may appreciate that numerous design configurations may be possible to enjoy the functional benefits of the inventive systems. Thus, given the wide variety of configurations and arrangements of embodiments of the present invention the scope of the invention is reflected by the breadth of the claims below rather than narrowed by the embodiments described above.

What is claimed is:

1. A slit maker, configured to make a slit in skin to receive a hair follicle; the slit maker comprising:
   a shaft, having a shaft central axis;
   a helix, mechanically coupled to the shaft;
   a tip at an end of the helix;
   an edge, beveled onto a distal end of the tip in a linear segment from a proximal end of the edge to an edge line wherein the edge is collinear with the edge line;
   an edge angle measured from the edge line to the shaft central axis; wherein the edge angle is at least 10 degrees but no more than 60 degrees.

2. The slit maker of claim 1, further comprising a first shaft bend section wherein the first shaft bend section has a first shaft bend entry central axis that is the same as the shaft central axis and a first shaft bend exit central axis that is rotationally offset from the shaft central axis by a shaft first angle; wherein the shaft first angle is at least 30 degrees but no more than 150 degrees.

3. The slit maker of claim 2, further comprising a shaft straight section joined to the first shaft bend section; wherein the shaft straight section has a central axis collinear with the first shaft bend exit central axis.

4. The slit maker of claim 3, further comprising a second bend section joined to the shaft straight section; wherein the second bend section has a second bend section entry central axis collinear to the first shaft bend exit central axis; wherein the second bend section has a second bend section exit central axis; wherein a second offset angle is measured from the first shaft bend exit central axis to the second bend section exit central axis; wherein the second offset angle is at least 90 degrees but no more than 180 degrees.

5. The slit maker of claim 1, wherein the helix further comprises a helical centroid which is part of helical plane; wherein the shaft central axis passes through the helical plane at a helical intersection angle; wherein the helical intersection angle is at least 45 degrees but no more than 135 degrees.

6. The slit maker of claim 1, wherein the edge extends from the edge line to a rounded edge at a sharpened angle that, when measured from the helix to the edge line along the rounded edge is at least 5 degrees but no more than 30 degrees.

7. The slit maker of claim 6, further comprising a rear side of the rounded edge which truncates to a point from a truncated tip; wherein a truncated tip angle is measured from a portion of the helix that extends to a back side; wherein the truncated tip angle is at least 30 degrees but no more than 90 degrees.

8. A slit maker, configured to make a slit in skin to receive a hair follicle; the slit maker comprising:
   a shaft, having a shaft central axis;
   a helix, mechanically coupled to the shaft;
   a tip at an end of the helix;
   an edge, beveled onto a distal end of the tip in a linear segment from a proximal end of the edge to an edge line; wherein the edge is collinear with the edge line;
   an edge angle measured from the edge line to the shaft central axis; wherein the edge angle is at least 130 degrees but no more than 170 degrees.

9. The slit maker of claim 8, further comprising a first shaft bend section wherein the first shaft bend section has a first shaft bend entry central axis that is the same as the shaft central axis and a first shaft bend exit central axis that is rotationally offset from the shaft central axis by a shaft first angle; wherein the shaft first angle is at least 30 degrees but no more than 150 degrees.

10. The slit maker of claim 9, further comprising a shaft straight section joined to the first shaft bend section; wherein the shaft straight section has a central axis collinear with the first shaft bend exit central axis.

11. The slit maker of claim 10, further comprising a second bend section joined to the shaft straight section;

wherein the second bend section has a second bend section entry central axis collinear to the first shaft bend exit central axis; wherein the second bend section has a second bend section exit central axis; wherein a second offset angle is measured from the first shaft bend exit central axis to the second bend section exit central axis; wherein the second offset angle is at least 90 degrees but no more than 180 degrees.

12. The slit maker of claim 8, wherein the helix further comprises a helical centroid which is part of helical plane; wherein the shaft central axis passes through the helical plane at a helical intersection angle; wherein the helical intersection angle is at least 45 degrees but no more than 135 degrees.

13. The slit maker of claim 8, wherein the edge extends from the edge line to a rounded edge at a sharpened angle that, when measured from the helix to the edge line along the rounded edge is at least 5 degrees but no more than 30 degrees.

14. The slit maker of claim 13, further comprising a rear side of the rounded edge which truncates to a point from a truncated tip; wherein an truncated tip angle is measured from a portion of the helix that extends to the back side; wherein the truncated tip angle is at least 30 degrees but no more than 90 degrees.

15. A process for making a slit on an eyelid in order to insert a hair follicle, the process comprising:

establishing a reference line that is parallel to and offset from a distal edge of the eyelid;
providing a slit maker further comprising:
   a shaft, having a shaft central axis;
   a helix, mechanically coupled to the shaft;
   a tip at an end of the helix;
   an edge, beveled onto a distal end of the tip in a linear segment from a proximal end of the edge to an edge line; wherein the edge is collinear with the edge line;
inserting the edge at a slit entrance point;
rotating the slit maker to create the slit having a slit central axis.

16. The process of claim 15, further comprising: creating a slit entrance angle measured from the reference line to the slit central axis wherein the slit entrance angle is at least 0 degrees but no more than 90 degrees.

17. The process of claim 16, wherein the slit entrance angle is about 12.5 degrees.

18. The process of claim 16, wherein the slit entrance angle is about 167.5 degrees.

19. The process of claim 15, further comprising: creating a slit entrance angle measured from the reference line to the slit central axis wherein the slit entrance angle is at least 90 degrees but no more than 270 degrees.

* * * * *